(12) United States Patent
Smith et al.

(10) Patent No.: US 8,808,385 B1
(45) Date of Patent: Aug. 19, 2014

(54) MECHANICALLY-ACTIVATED SHAPE MEMORY POLYMER SPINAL CAGE

(71) Applicant: MedShape, Inc., Atlanta, GA (US)

(72) Inventors: Kathryn Smith, Atlanta, GA (US);
Kenneth A. Gall, Atlanta, GA (US);
Kenneth Dupont, Atlanta, GA (US)

(73) Assignee: MedShape, Inc., Atlanta, GA (US)

(*) Notice: Subject to any disclaimer, the term of this patent is extended or adjusted under 35 U.S.C. 154(b) by 141 days.

(21) Appl. No.: 13/735,027

(22) Filed: Jan. 6, 2013

(51) Int. Cl.
*A61F 2/44* (2006.01)

(52) U.S. Cl.
USPC ...................................... 623/17.16; 623/17.11

(58) Field of Classification Search
USPC ............. 606/246–249, 279; 623/17.11–17.16
See application file for complete search history.

(56) References Cited

U.S. PATENT DOCUMENTS

| 5,002,563 | A | 3/1991 | Pyka et al. |
| 5,676,175 | A | 10/1997 | Bar et al. |
| 5,779,707 | A | 7/1998 | Bertholet et al. |
| 5,964,744 | A | 10/1999 | Balbierz |
| 6,113,611 | A | 9/2000 | Allen et al. |
| 6,579,305 | B1 | 6/2003 | Lashinski |
| 6,637,995 | B1 | 10/2003 | White |
| 6,663,664 | B1 | 12/2003 | Pacetti |
| 7,556,647 | B2 | 7/2009 | Drews et al. |
| 8,069,858 | B2 | 12/2011 | Gall |
| 2003/0208211 | A1 | 11/2003 | Kortenbach |
| 2009/0192615 | A1* | 7/2009 | Tyber et al. ................. 623/17.16 |
| 2009/0248141 | A1 | 10/2009 | Shandas |
| 2010/0249932 | A1* | 9/2010 | Trieu et al. ................. 623/17.11 |

FOREIGN PATENT DOCUMENTS

| EP | 1481640 | 1/2004 |
| EP | 1607048 | 12/2005 |
| WO | WO9213490 | 8/1992 |
| WO | WO2006108114 | 10/2006 |
| WO | WO2008034277 | 3/2008 |
| WO | WO2008051254 | 5/2008 |
| WO | WO2009050717 | 4/2009 |

* cited by examiner

*Primary Examiner* — Mary Hoffman
*Assistant Examiner* — Christina Negrellirodriguez
(74) *Attorney, Agent, or Firm* — Furman IP Law

(57) ABSTRACT

Provided herein are shape memory polymer spinal cages including polymers with intended deployment at temperatures far below the onset of the glassy transition of the shape memory polymer. The described shape memory polymer spinal cages are adapted to be deployed by mechanical activation rather than thermal activation or activation by other stimuli. Thus, the shape memory polymers used herein are configured to have transition temperatures far above their temperatures of intended use, thereby requiring mechanical activation to recover stored strains.

20 Claims, 10 Drawing Sheets

MECHANICALLY-ACTIVATED SHAPE MEMORY POLYMER SPINAL CAGE

FIELD OF THE TECHNOLOGY

Embodiments of this disclosure relate to shape memory polymer spinal cages and configurations thereof.

SUMMARY OF THE DESCRIPTION

Provided herein are shape memory polymer spinal cages including polymers with intended deployment at temperatures far below the onset of the glassy transition of the shape memory polymer. The described shape memory polymer spinal cages are adapted to be deployed by mechanical activation rather than thermal activation or activation by other stimuli. Thus, the shape memory polymers used herein are configured to have transition temperatures far above their temperatures of intended use, thereby requiring mechanical activation to recover stored strains.

In one aspect, the disclosure describes a spinal cage system including a spinal cage with a body made of a shape memory polymer with a stored strain, wherein the shape memory polymer has a transition onset temperature above 120 degrees Fahrenheit. The stored strain comprises a difference in shape between an insertion shape of the body having an insertion axis and a deployed shape of the body adapted to cover a central intervertebral space. The spinal cage system includes a detachable deployment mechanism that connects with the body along the insertion axis at an insertion-leading portion of the body and at an insertion-trailing portion of the body. The deployment mechanism is adapted to activate recovery within a plurality of portions of the shape memory polymer only with mechanical forces applied along the insertion axis between the insertion-leading portion and the insertion trailing portion. The shape memory polymer is adapted to expand via only thermal expansion below 120 degrees Fahrenheit and without undergoing any shape memory polymer activation.

In another aspect, the disclosure describes a method including steps of shaping a spinal cage from a shape memory polymer with a transition temperature above 120 degrees Fahrenheit and imparting a stored strain on the shape memory polymer. The method further includes forming holes in a vertical wall of the spinal cage along an insertion axis of the spinal cage, the holes adapted to receive a deployment mechanism adapted to provide deployment forces along the insertion axis to activate recovery of the stored strain in the spinal cage. The method further includes storing the spinal cage with the stored strain in a sterile package below 120 degrees Fahrenheit.

In another aspect, the disclosure describes a surgical method including the steps of receiving a spinal cage formed of a shape memory polymer with a transition onset temperature above 120 degrees Fahrenheit and containing a stored strain defining a difference between an expanded shape and an insertion shape. The method further includes inserting the spinal cage in the insertion shape into an intervertebral space along an insertion axis of the spinal cage and engaging a deployment mechanism with the spinal cage to apply a deployment force to the spinal cage along the insertion axis. The method further includes applying the deployment force to the spinal cage along the insertion axis to activate the shape memory polymer to recover the stored strain while the shape memory polymer remains below the transition onset temperature. In the method, the applying the deployment force is performed with the shape memory polymer being below the transition onset temperature. The method further includes removing the deployment mechanism from the spinal cage in the expanded shape while the shape memory polymer is below the transition onset temperature.

Other embodiments and features of the present disclosure will be apparent from the accompanying drawings and from the detailed description that follows.

BRIEF DESCRIPTION OF THE DRAWINGS

The embodiments are illustrated by way of example and not limitation in the Figures of the accompanying drawings in which like references indicate similar elements.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one. Reference in this specification to "one embodiment" or "an embodiment" or the like means that a particular feature, structure, or characteristic described in connection with the embodiment is included in at least one embodiment of the disclosure. The appearances of the phrase "in one embodiment" or the like in various places in the specification are not necessarily all referring to the same embodiment, nor are separate or alternative embodiments mutually exclusive of other embodiments. Moreover, various features are described that may be exhibited by some embodiments and not by others.

Figure 1:
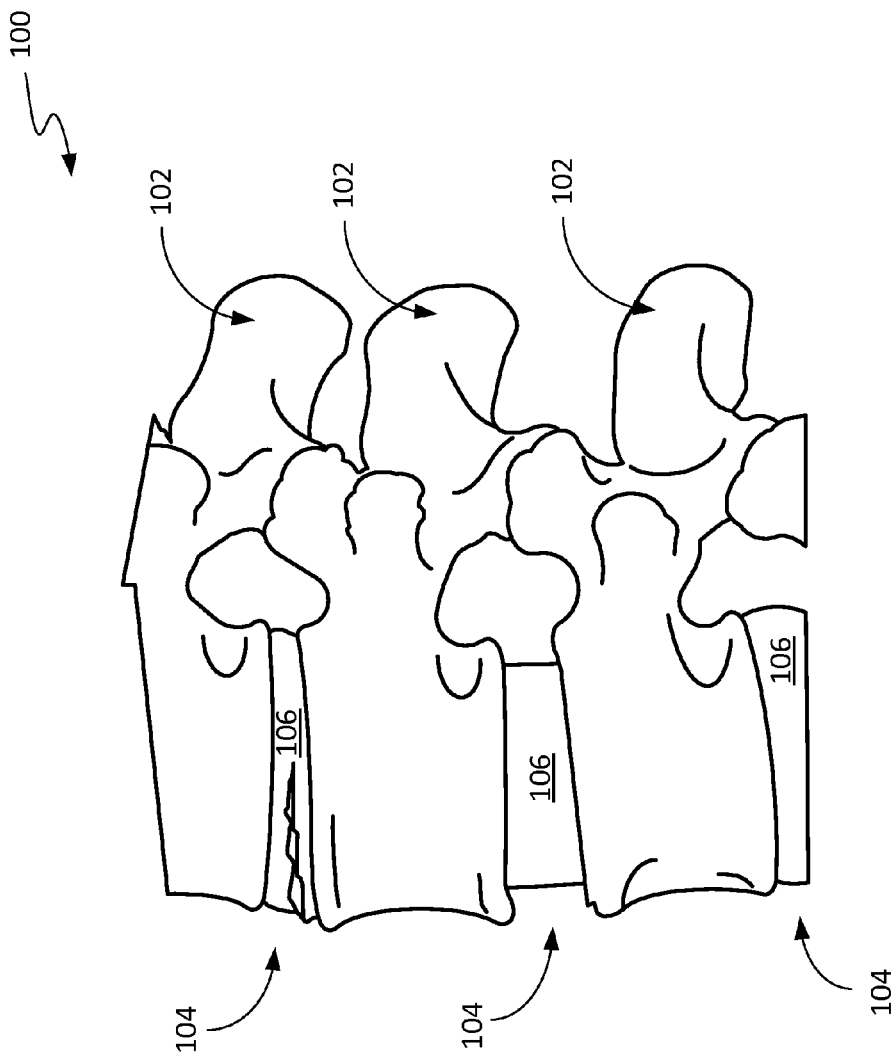
FIG. 1 shows a human spine in which an exemplary embodiment of a spinal cage may be used.

FIG. 1 shows a human spine in which an exemplary embodiment of a spinal cage may be used. The spine 100 includes multiple vertebrae 102 with intervertebral spaces 104 containing discs of the spine 106. The discs 106 may become ruptured by injury or weakened by disease or degeneration, as illustrated by the defects shown in the top disc.

As a surgical treatment, a spinal cage may be inserted within the affected intervertebral space 104 for the purpose of fusing two or more vertebrae 102 together. Spinal fusion may be used where one or more spinal discs 106 have degenerated or ruptured recurrently. As is common practice, spinal cages may be inserted into the spine 100 through various procedures commonly known as ALIF, PLIF, and TLIF procedures. Although several embodiments are described herein with respect to TLIF procedures, the spinal cages and techniques described herein may be adapted to other spinal fusion procedure types.

To accomplish the goal of fusing certain vertebrae 102 of the spine, the spinal cages described herein may be installed with bone cement, a demineralized bone matrix, and/or other bone growth agents in order to facilitate fusion of the vertebrae. Although these bone growth agents may be included in many of the described techniques and may be used with the described spinal cages, the details of this use of bone growth agents is not described herein in order to focus on the inventive aspects of the spinal cage and related techniques that are the subject of this disclosure.

Figure 2:
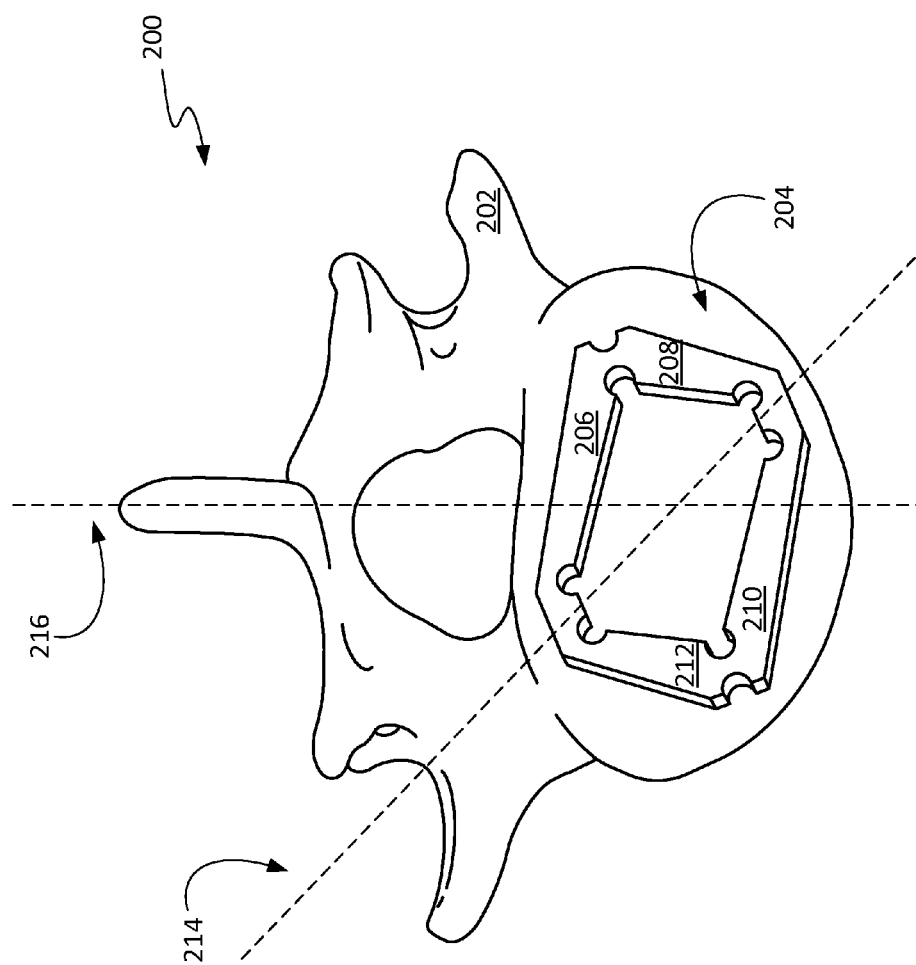
FIG. 2 shows an exemplary embodiment of a TLIF spinal cage placement between adjacent vertebral bodies.

FIG. 2 shows an exemplary embodiment of a TLIF spinal cage placement between adjacent vertebral bodies. The exemplary TLIF spinal cage is shaped in its deployed shape to cover a majority of the intervertebral space. The exemplary spinal cage 204 is shown inferior to a superior vertebra 202 of the intervertebral space as placed with the body of the spinal cage in a deployed shape, such as after installation and deployment of all of the stored strain in the spinal cage has completed. As described further herein, this deployed shape corresponds to a shape of the shape memory polymer in the spinal cage with no stored strain, namely after recovery of all the strain stored in the body of the device. The deployed shape may be referred to herein as the expanded shape, the memorized shape, the unconstrained shape, or the original shape.

The TLIF procedure installs the spinal cage 204 along an insertion axis 214 that is 35 degrees offset from the sagittal plane 216 of the human patient. As described further herein, the surgical installation procedure for the TLIF spinal cage may require a cross-section smaller than a 1 cm by 1 cm square as measured perpendicular to the insertion axis 214.

The deployed shape of the exemplary TLIF spinal cage 204 has four major side walls, including, as referenced to the surgical patient's spine, a dorsal side wall 206, a right side wall 208, a ventral side wall 210, and a left side wall 212. The four side walls 206, 208, 210 and 212 are formed in the body of the spinal cage 204 as a loop roughly with the deployed shape of a parallelogram with the side walls connected at corner sections. In addition, the TLIF spinal cage 204 has a top side surface and bottom side surface adapted to interface with the surfaces of the vertebrae 202 that define the intervertebral space.

The insertion axis 214 is exemplary in showing insertion inferior to the shown vertebra 202 from the patient's left side. In other embodiments, insertion may come from the patient's right side, and the designations of right and left for the side walls 208 and 212 would commensurately be reversed. In other embodiments described herein, the right and left side walls are reversed and therefore right and left designations are meant only to illustrate one surgical delivery method. In embodiments where a direction is shown or described, appropriate adjustment of which side of the spinal cage is described and may be understood by placing the longer sides of the spinal cage at the deployed position of the dorsal side wall 206 and the ventral side wall 210. Furthermore, as described further herein, deployment of the spinal cage using a deployment mechanism applying forces roughly along the insertion axis 214 may be understood to expand the side walls 206, 208, 210, and 212 from a position in the spinal cage's collapsed shape into the side walls' positions in the spinal cage's deployed shape.

Figure 3:
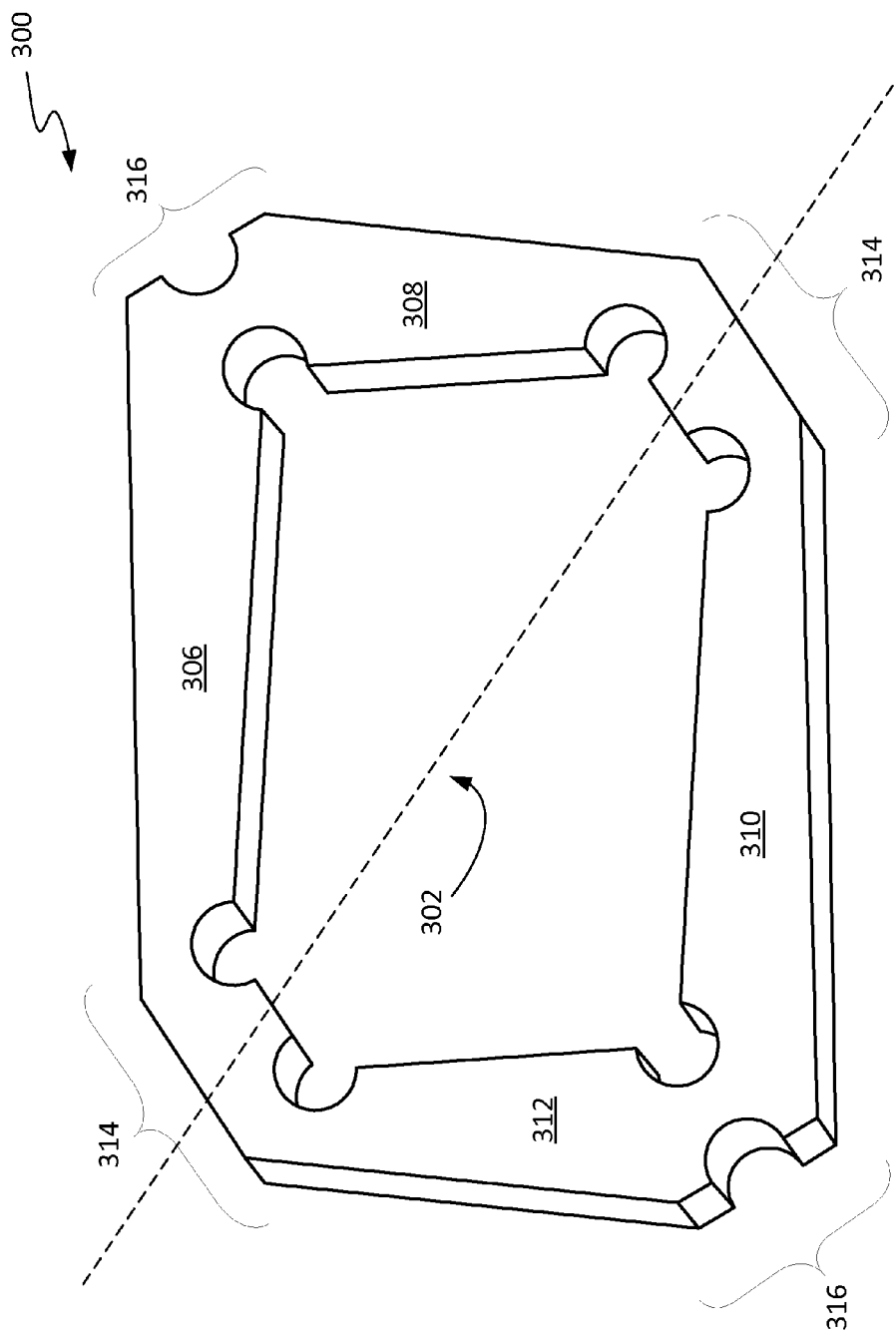
FIG. 3 shows an exemplary embodiment of a TLIF spinal cage in a shape with no stored strain.

FIG. 3 shows further details of the exemplary embodiment of a TLIF spinal cage 300 in a deployed shape with no stored strain, including cutout details of the deployed shape of the embodiment related to storing strain in an installation shape of the spinal cage. The TLIF spinal cage 300 has a roughly parallelogram shape in its deployed shape. The spinal cage 300 has a dorsal side wall 306, a right side wall 308, a ventral side wall 310, and a left side wall 312.

The spinal cage 300 has an insertion axis 302 and the spinal cage is shown oriented for insertion into a patient from the patient's left side. The insertion axis 302 is roughly defined along a diagonal of the installation shape between the corner regions 314. As described further herein, deformation of the spinal cage 300 is created by compressing the opposite corner regions 316 toward the insertion axis 302, thereby moving each of the side walls 306, 308, 310, and 312 toward alignment with the insertion axis.

This deformation procedure imparts strain into the TLIF spinal cage 300 that is concentrated in the corner regions 314 and 316. Thus, interior cutouts and exterior cutouts are provided in the exemplary embodiment of the TLIF spinal cage to allow the concentrated strain to be stored in thinner sections of the spinal cage without reducing the width of the side walls 306, 308, 310, or 312. The cutouts may be adjusted as necessary to allow for deformations that are required to reduce the cross-section of the spinal cage to a profile of less than 1 cm by 1 cm. For example, in one embodiment, the spinal cage has a cutout pattern that places two adjacent semi-circular interior cutouts at the corner regions 314 (e.g., opposing junctions of side walls that lie along the insertion axis). In this embodiment, the corner regions 316 have both an interior cutout and an exterior cutout, thus allowing strains of the deformation to be withstood by the shape memory polymer spinal cage.

Figure 4:
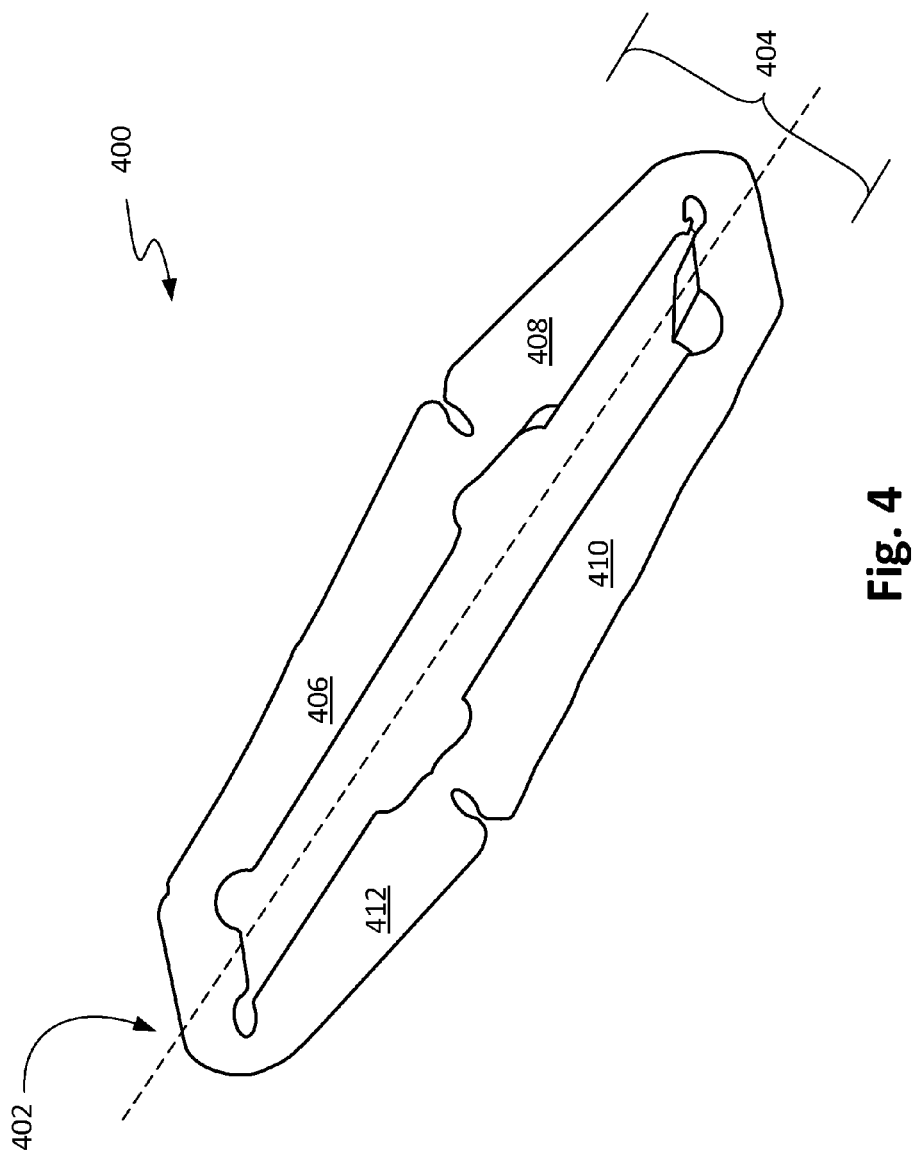
FIG. 4 shows an exemplary embodiment of a TLIF spinal cage in a collapsed shape with an insertion stored strain having been imparted to the TLIF spinal cage.

FIG. 4 shows an exemplary embodiment of a TLIF spinal cage 400 with a stored strain having been imparted to the shape memory polymer and stored in a deformed shape of the spinal cage. The deformed shape may be referred to herein as the insertion shape, the installation shape, the collapsed shape, the strained shape, the storage shape, or the temporary shape. The deformed shape, and the strain stored thereby, may both vary from spinal cage to spinal cage, however, the measured cross-section across the insertion axis 402 is preferably consistent within a cross-section 1 cm by 1 cm, such as to fit within a surgical portal of a TLIF procedure. Other surgical procedures and surgical portals may be used, thereby requiring different cross-sections of the spinal cage, and therefore this example of the TLIF procedure is not meant to limit the application of this disclosure.

The orientation of this embodiment of the spinal cage 400 is shown to allow insertion from the patient's left side through the surgical portal, although the spinal cage may be inserted through other sides and/or portals. Accordingly, for this embodiment, the insertion axis 402 is shown rotated roughly 35 degrees from the sagittal plane for the exemplary TLIF procedure. Thus, the spinal cage 400 and insertion axis 402 are shown oriented similarly to the spinal cage 300 shown in FIG. 3. Other angles and procedures may be used, as described further herein.

The exemplary TLIF spinal cage 400 is deformed to produce the shown insertion shape of the shape memory polymer. This deformed shape has a lateral dimension 404 and a vertical dimension (into the drawing plane) that are both approximately equal to 1 cm or less than 1 cm, as required by the particular surgical portal and technique used. By deforming the TLIF spinal cage 400 with this stored strain, the dorsal side wall 406, the right side wall 408, the ventral side wall 410, and the left side wall 412 are aligned closely with the insertion axis 402 as compared to the deployed shape of the spinal cage.

As shown, the spinal cage 400 is oriented for insertion from the patient's left side. The junction region between ventral side wall 410 and right side wall 408 is inserted as the insertion-leading point of the collapsed spinal cage 400 through a surgical portal on the patient's left side. As described further herein, deployment of the collapsed spinal cage 400 through recovery of the stored strain in the shape memory polymer is accomplished via applying compressive forces applied to the junction regions and generally along the insertion axis 402. Stored strain is concentrated in the junction regions between the side walls 406, 408, 410, and 412 and the compressive forces on the junction regions along the insertion axis 402 act to transform the spinal cage 400 from the compressed parallelogram shape of the insertion shape to the expanded parallelogram shape of the deployed spinal cage.

As used herein the term stored strain is a difference in shape of a portion of shape memory polymer (e.g., a portion of the spinal cage 400) between an insertion shape and a deployed shape. The stored strain of the entire spinal cage may be understood as describing the entire difference in shape between the insertion shape of the spinal cage 400 and the deployed shape of the spinal cage (shown in FIG. 3), which includes a summation of the stored strains in each portion of the spinal cage.

Figure 5:
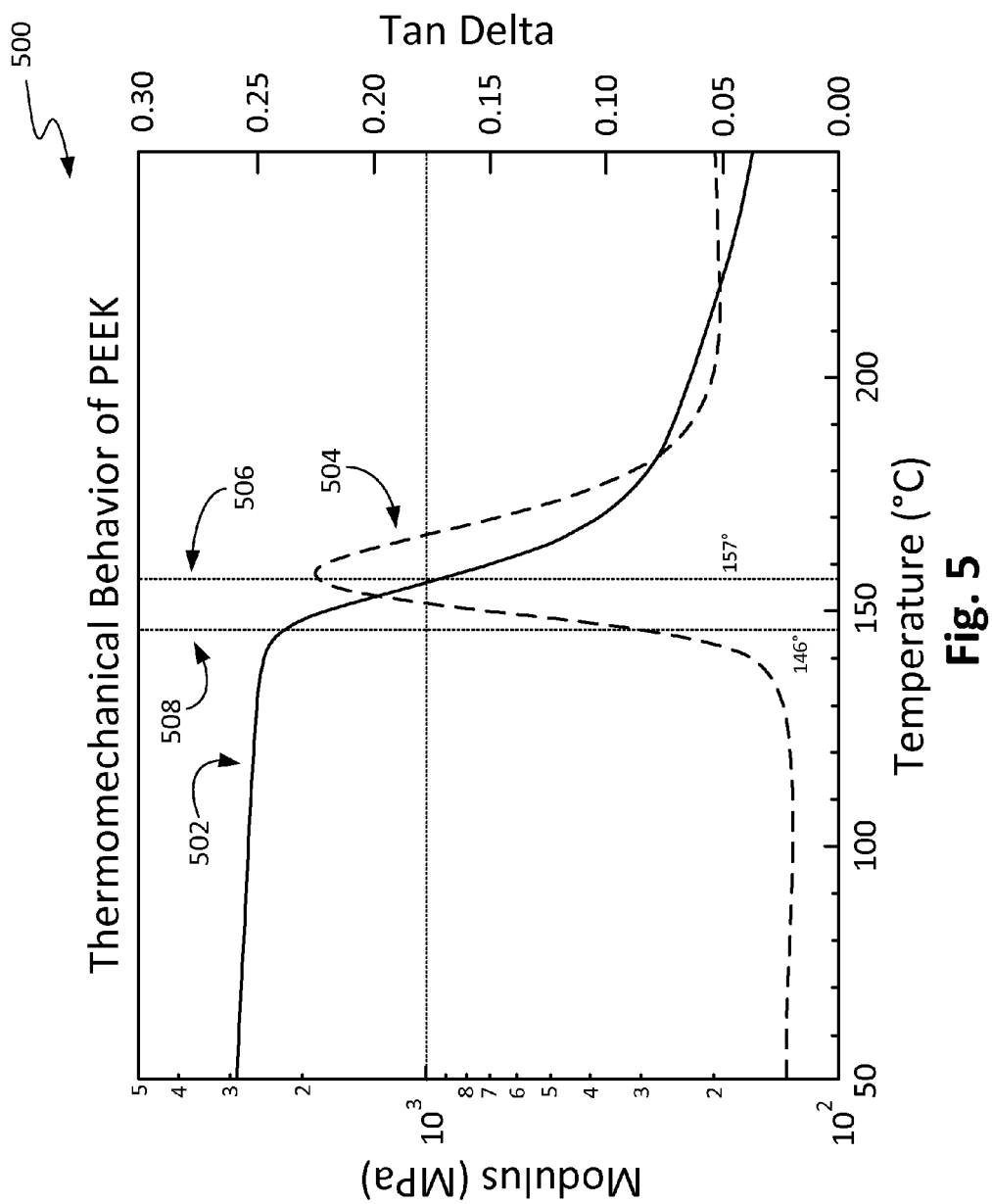
FIG. 5 shows a dynamic mechanical analysis plot of an exemplary embodiment of a shape memory polymer, namely poly-ether ether ketone or PEEK.

FIG. 5 shows a dynamic mechanical analysis plot 500 of an exemplary embodiment of a shape memory polymer, namely poly-ether ether ketone or PEEK. Shown in the graph 500 is modulus curve 502 produced by dynamic mechanical analysis of PEEK over a temperature range from 50 degrees Celsius to 250 degrees Celsius. The modulus curve 502 shows a glassy modulus at 2.7 gigapascals (GPa), which transitions as temperature is increased to a rubbery modulus approximately between 200-400 megapascals (MPa). A transition onset temperature 508 is shown at the point in the plateau where the transition from the glassy state of the polymer begins to transition to the rubbery state of the polymer and corresponds to 146 degrees Celsius (or 294.8 degrees Fahrenheit). The tan delta curve 504 is defined by the phase lag between the stress and strain of the polymer in the DMA analysis. A glass transition temperature 506, as the term is used herein, is defined at the peak of the tan delta curve, and corresponds to 157 degrees Celsius (or 314.6 degrees Fahrenheit) for the exemplary embodiment of PEEK. Other shape memory polymers may have similar mechanical properties and commensurate glass transition temperatures above 300 degrees Fahrenheit and transition onset temperatures above 285 degrees Fahrenheit.

The exemplary shape memory polymer PEEK described herein includes high glass transition and transition onset temperatures, which may change depending on the selection of polymer. As described herein, the embodiment of PEEK has a transition onset temperature exceeding human body temperature by almost 200 degrees Fahrenheit. Other shape memory polymers may have lower transition temperatures and lower transition onset temperatures that are closer to the human body temperature, yet still these temperatures may be prohibitively high such that thermal activation of the shape memory polymer difficult or impossible without causing tissue necrosis around the shape memory polymer. By using mechanical activation, many more shape memory polymers may thus be considered for use in the spinal cage because there are no restrictions requiring the shape memory polymer to have a lower temperature such that significant thermal management is not required. Any of these shape memory polymer choices may be selected without concern of a high transition onset temperature, such as selecting based on other properties of the shape memory polymer like modulus, hardness, etc. Instead, these other shape memory polymer spinal cages may be installed using mechanical activation, as described further herein, in order to safely activate the shape memory polymer without the risks of tissue necrosis.

Tissue necrosis begins very close to normal human body temperature, so thermal activation even as low as 20 degrees Fahrenheit above human body temperature (e.g., 118.6 degrees Fahrenheit) can prove troublesome if the spinal cage device is in close proximity to human body tissues during activation. Therefore, shape memory polymers may be advantageously used with mechanical activation even though the shape memory polymer has onset transition temperatures 20, 30, 40, 50 degrees Fahrenheit, or more above human body temperature. For example, a shape memory polymer with a transition onset temperature above 120 degrees Fahrenheit provides a difference of greater than 20 degrees Fahrenheit over the normal human body temperature of 98.6 degrees Fahrenheit.

By activating a shape memory polymer below the transition onset temperature, which may be just below the transition onset temperature, close to the transition onset temperature (e.g., 5, 10, 20, 30 degrees Fahrenheit below), or 100 or more degrees Fahrenheit below the transition onset temperature, whereby such decisions for selecting shape memory polymers may be made irrespective of transition onset temperature.

As described further herein, a shape memory polymer responds only through thermal expansion (or contraction) below the transition onset temperature. Below this temperature, a shape memory polymer remains not activated by thermal activation. Unless and until the shape memory polymer is activated, such as via mechanical activation forces being applied as described further herein, the device responds to fluctuations of temperature via conventional thermal expansion.

Conventionally understood thermal expansion and the shape changes caused thereby (e.g., volumetric changes) should not be confused herein with the description of activation of a shape memory polymer. In many instances, thermal expansion occurs to a much smaller extent than activation or recovery of stored strain in a shape memory polymer, based largely on the extent of stored strains often imparted into shape memory polymers. However, thermal expansion will occur at temperatures far below shape memory activation. Thermal expansion below the glass transition temperature should not be confused, therefore, with changes in shape that occur due to stored strain recovery.

The specific properties of the particular PEEK shape memory polymer described herein and measured in the graph 500 include a glassy modulus of 2.7 GPa (+/−0.1), a transition onset temperature of 146 degrees Celsius (+/−0.1), a glass transition temperature of 157 degrees Celsius (+/−0.1), and a transition temperature range measured 24 degrees Celsius. Other varieties of PEEK or other tough shape memory polymers may include a glassy modulus of around 2-4 GPa, and a glass transition temperature of around 100-170 degrees Celsius.

As described further herein, the shape memory polymer PEEK may be used in a spinal cage to provide both a collapsed shape of the spinal cage that is advantageous for insertion through the surgical portal as well as an expanded shape of the spinal cage that is advantageous for fusing vertebrae. As shown in FIGS. 2-4, the different shapes require significant deformations of the spinal cage, including substantial stored strains. Therefore, using the shape memory properties of the shape memory polymer allows large deformations and stored strains, while also providing for recovery of these strains.

Stored strains may be set above or below the glass transition temperature. In one embodiment, a stored strain is set above a glass transition temperature via heating the shape memory polymer above its glass transition temperature, straining the shape memory polymer (e.g., imparting the strain to be stored), and thereafter storing the strain via maintaining the imparted strain while cooling the shape memory polymer below its glass transition temperature. In other embodiments, the strain may be imparted and set (e.g., stored) in the shape memory polymer via deforming the shape memory polymer below the glass transition temperature. After the strain is imparted, the strain is set and stored immediately in the shape memory polymer based on the temperature remaining below the glass transition temperature.

The shape memory polymer PEEK is described herein as an exemplary embodiment of a shape memory polymer with a high glass transition temperature and a corresponding high glassy modulus. Other shape memory polymers may be substituted for PEEK, consistent with the properties described herein including operation of the shape memory polymer spinal cage via mechanical activation at temperatures far below both the glass transition temperature and the transition onset temperature.

Previous spinal cages may have relied on thermal activation or other external stimulus to activate shape memory recovery of stored strain in the spinal cages. However, thermal activation has significant downsides for surgery. Shape memory polymers with high glassy moduli or otherwise very tough shape memory polymers also tend to have high glass transition temperatures. Consequently the temperatures needed to transition these tough shape memory polymers with high glassy moduli and high glass transition temperatures can make surgical installation of a spinal cage dangerous to perform near surrounding tissues without considerable chance of damaging or killing the surrounding tissue.

The exemplary embodiment of PEEK is an example of a shape memory polymer with a high transition onset temperature and a corresponding high glass transition temperature. Both the glass transition temperature of PEEK and the transition onset temperature of PEEK are more than 100 degrees Celsius over temperatures that kill living tissues. Heating the spinal cage or other instruments to either the glass transition onset temperature (i.e., 294.8 degrees Fahrenheit) or the glass transition temperature (i.e., 314.6 degrees Fahrenheit) will cause burning or other tissue necrosis extremely quickly. Therefore, using this shape memory polymer with its intended thermal activation would be disadvantageous in surgical applications.

Instead, shape memory recovery of any stored strain during surgery by the spinal cages described herein is accomplished via mechanical activation rather than via any heating to cause temperature activation or via any other form of activation (e.g., radiation, electromagnetic coupling).

Mechanical activation causes recovery of the stored strain within a shape memory polymer without applying any thermal energy or heating the shape memory polymer to a temperature above the surrounding or ambient temperature (e.g., a patient's body temperature). For example, the temperature of the spinal cage as well as the temperatures of the instruments and surrounding body tissue during the surgical procedure may be kept at a lower temperature than the transition onset temperature because thermal activation is not used during the surgery. In addition, complicated heating mechanisms or techniques are not used as part of the installation and deployment of the spinal cage. A mechanical activation deployment mechanism may be used instead, as described further herein, thereby simplifying the surgical procedure considerably.

The described PEEK shape memory polymer has a significantly high glassy modulus, namely 2.7 GPa. The glassy modulus of the PEEK is exhibited while installed in the body due to the body temperature (e.g., approximately 37 degrees Celsius) being significantly lower than both the glass transition temperature (157 degrees Celsius) and the transition onset temperature (146 degrees Celsius). By using mechanical activation of stored strain within the shape memory polymer, deploying the shape memory polymer may be performed while the shape memory polymer remains with a modulus above 2.5 GPa, namely without transitioning above the glass transition temperature and into the rubbery modulus. Further, the additional processes of forming the body of the spinal cage and imparting the stored strain may also be performed below the glass transition temperature and while the shape memory polymer exhibits a high modulus such as above 2.5 GPa, or in the case of the PEEK shape memory polymer, around 2.7 GPa.

Figure 6:
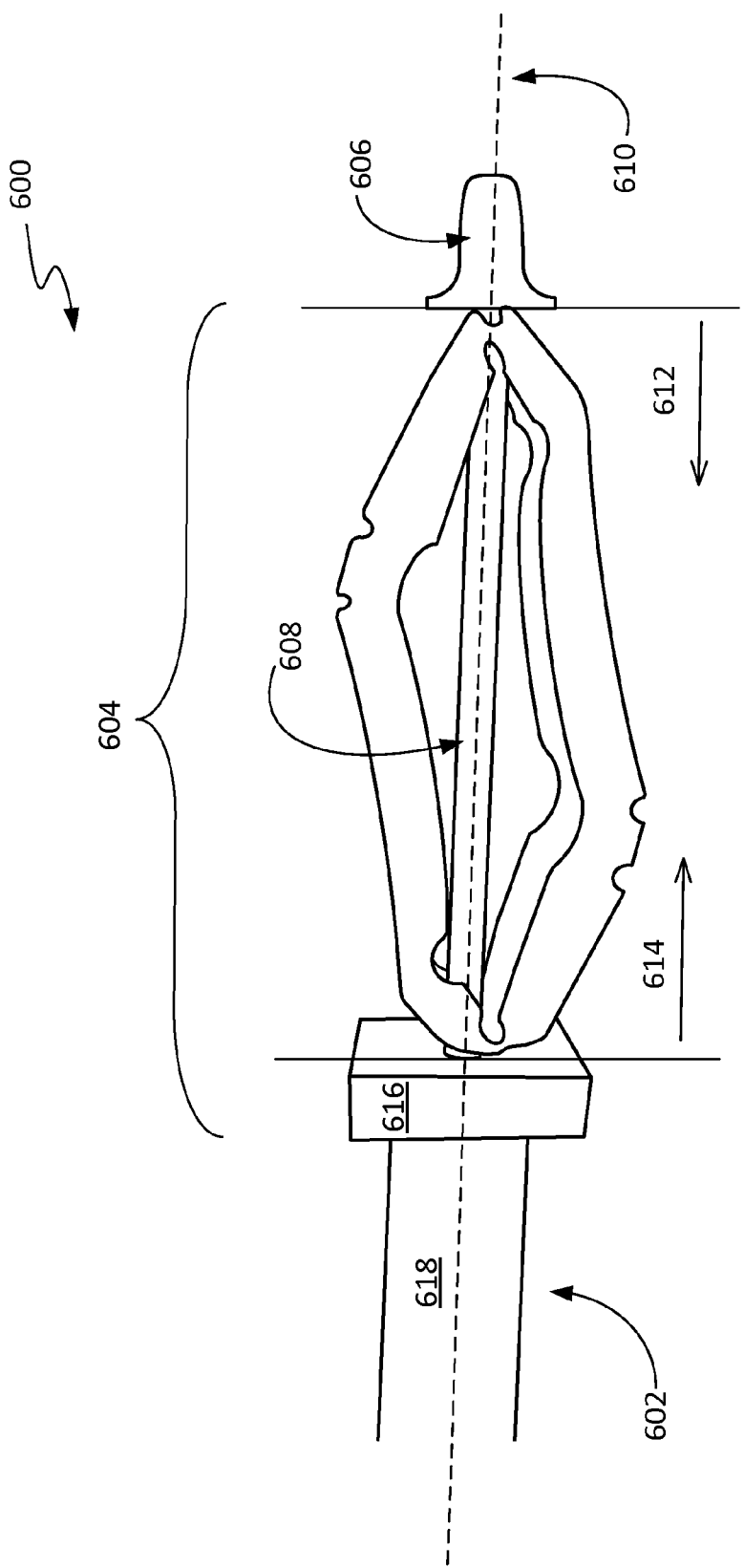
FIG. 6 shows a top view of an exemplary embodiment of a TLIF spinal cage in a collapsed shape with a deployment mechanism inserted through a vertical wall of the spinal cage.

FIG. 6 shows a top view of an exemplary embodiment of a TLIF spinal cage in a collapsed shape with a deployment mechanism inserted through a vertical wall of the spinal cage. The spinal cage 600 is attached to a deployment mechanism 604, including compression rod 608, insertion tip 606, and back plate 616. The deployment mechanism 604 is carried and/or supported by the insertion rod 618, which is part of an insertion tool 602 that aids insertion of the spinal cage along or nearly along the insertion axis 610. The deployment mechanism 604 includes a back plate 616 that may help drive the assembly into position, such as through a surgical portal into a prepared intervertebral space. The deployment mechanism 604 has an insertion tip 606 connected by a compression rod 608 that helps guide the assembly through the surgical portal to the intervertebral space. The insertion tip 606 also allows the compression rod 608 to provide compressive forces 612 and 614 along the insertion axis 610 for deploying the spinal cage via mechanical activation.

In this simplified model of the deployment mechanism 604, the compression rod 608 is drawn into the insertion rod 618 in order to create the compressive forces 612 and 614. Other embodiments of a deployment mechanism 604 may be used to create the compressive forces 612 and 614. These compressive forces 612 and 614 may be more generally described further herein as deployment forces due to their use in mechanically deploying the shape memory polymers herein through mechanical activation. In addition, expansive forces may also be used to recover stored strain using other embodiments of the deployment mechanism, including through the translation of forces through the body of the spinal cage, as described further herein.

In one embodiment of the deployment mechanism 604 and the connected spinal cage are driven through the surgical portal into the intervertebral space using the insertion tool 602. Insertion forces for inserting the spinal cage 600 may be provided via pushing the spinal cage against the back plate 616 using the insertion rod 618. Alternatively or additionally, the insertion tip 606 may be attached to the spinal cage 600 and provide insertion forces through pulling the spinal cage into the intervertebral space.

While the spinal cage is inside the intervertebral space, the compression rod 608 and insertion tip 606 are retracted through the back plate 616, causing compression of the spinal cage along the insertion axis through compressive forces 612 and 614. These compressive forces 612 and 614 cause mechanical activation of the stored strain in the spinal cage in its compressed shape. Surgical processes are described in detail further herein for deployment of the spinal cage via mechanical activation of the stored strain in the spinal cage.

The interfaces between the spinal cage 600, the back plate 616, and the insertion tip 606 are shown simply pressing against the spinal cage in opposing directions 612 and 614. In other embodiments, the insertion tip 606 and/or the back plate 616 may be connected to the spinal cage, such as through screw threads or locking mechanisms to allow the spinal cage to have other forces imparted on the spinal cage during insertion. In the embodiment shown, the connections are simplified to highlight the compressive forces applied roughly along the insertion axis (e.g., in directions 612 and 614) that are used to cause the activation of the shape memory polymer and recovery of the strain stored therein.

An important feature of the spinal cage 600 is the ability to deform to its deployed shape under the compressive forces 612 and 614, rather than through thermal activation. As described further herein, very tough shape memory polymers with high moduli have corresponding high transition temperatures, making them unsuitable for thermal activation because thermal activation at high temperatures inside the body is either impossible or requires significant measures be taken to protect the surrounding tissues. The mechanically-activated spinal cage, by contrast, activates without thermal activation and activates, instead, without any heating beyond the surrounding temperatures of the surgical process. For example, the spinal cage can be mechanically-activated at a deployment temperature that is the patient's body temperature, a surrounding temperature of the surgical environment, such as the temperature of a saline bath or room temperature, or at some intermediate temperature, without approaching a temperature at which thermal activation would start. In addition, no complicated measures to get other activating stimuli must be employed.

Instead, as shown in FIG. 6, a simple mechanism, such as compression rod 608 inserted through the spinal cage 600, may be used to mechanically activate the spinal cage. As will be comprehended by those skilled in the art, additional mechanisms may be adapted to apply the compressive forces 612 and 614 or other forces (e.g., expansive forces perpendicular to the insertion axis 610) in order to activate the spinal cage 600.

Furthermore, the mechanically-activated spinal cage activates into its deployed shape with lower forces required during activation than a similar device that had no stored strain in the deformed shape. Instead, the recovery of the stored strain is accomplished with forces of a much smaller magnitude than those required to impart strain on the spinal cage. Initially straining a shape memory polymer with a high modulus such as PEEK may be impossible in many surgical procedures without complicated mechanisms for providing the initial straining forces.

In addition, after recovering the stored strain, a fully-deployed mechanically-activated spinal cage has no strain, having been returned to its original unstrained shape. This configuration is stronger than a configuration of a prior art spinal cage that has strain imparted to the spinal cage during installation. In other words, if a prior art spinal cage were inserted without strain and thereafter strained to its final shape, the final shape would contain unreleased strain. Such a configuration with unreleased strain can continue to exert forces/stresses toward returning the spinal cage to its unstrained shape, which could weaken, degrade and eventually destroy the connection with the vertebrae and require further surgical intervention.

Figure 7:
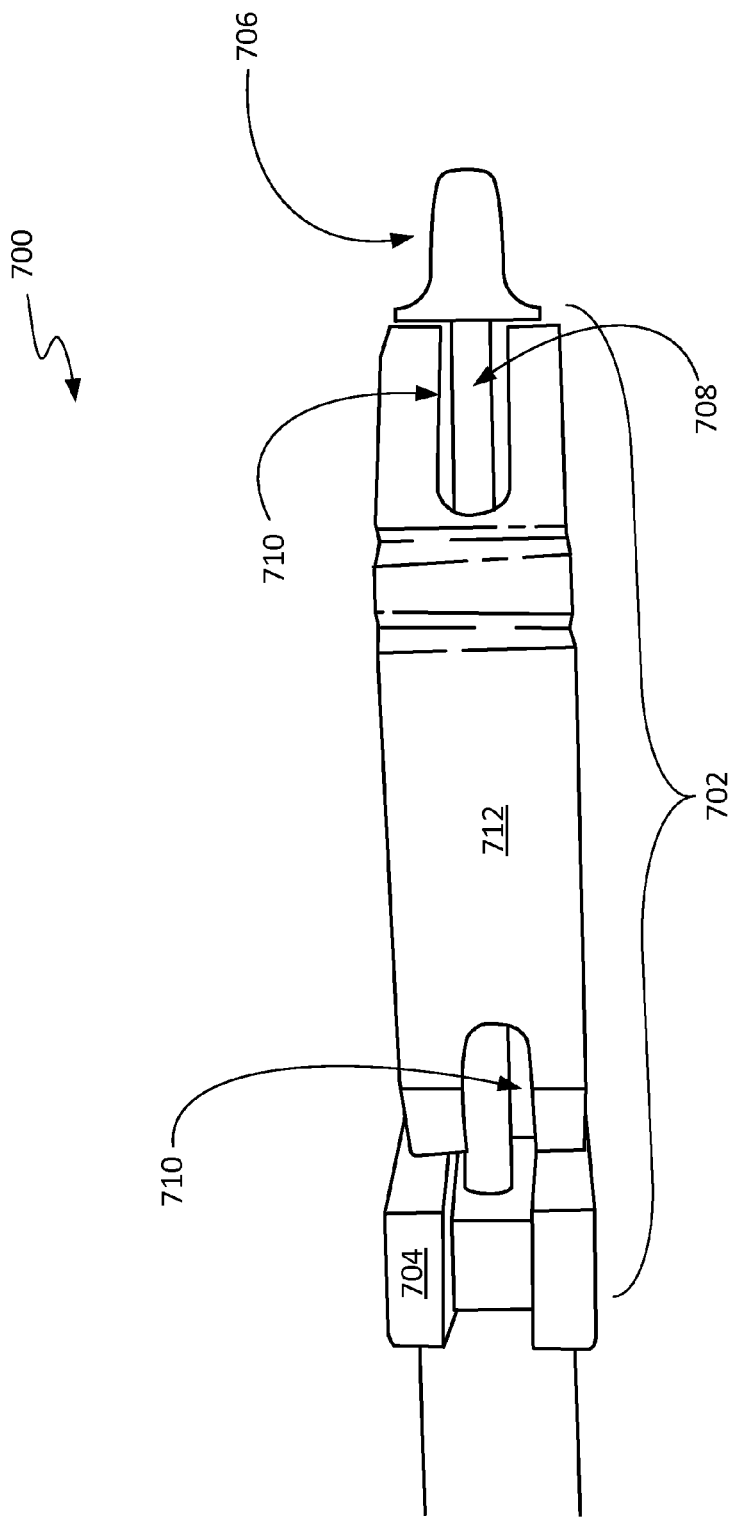
FIG. 7 shows a side view of another exemplary embodiment of a TLIF spinal cage in a collapsed shape with a deployment mechanism inserted through a vertical wall of the spinal cage, showing exemplary slot cutout portions of the spinal cage.

FIG. 7 shows a side view of another exemplary embodiment of a TLIF spinal cage 700 in a collapsed shape with a deployment mechanism 702 inserted through the vertical faces 712 of the side walls of the spinal cage. The deployment mechanism 702 is shown passing through exemplary slot cutout portions 710 (e.g., holes) formed in the spinal cage 700. Particularly, compression rod 708 passes through the holes or slot cutout portions 710 of the spinal cage 700 to attach to the insertion tip 706 and to pass through the back plate 704.

The slot cutout portions are cut as slots to allow the spinal cage side walls to expand in a lateral direction (i.e., into/out of the plane of the page). The side walls move during deployment, such that, in the exemplary embodiment approximating a parallelogram, the angles of the corners along the insertion axis increase toward the expanded non-deformed shape of the spinal cage. In other embodiments, other cutouts may be formed to allow such movement toward the deployed shape, while the compression rod 708 is thereby allowed to move freely during deployment and may take different shapes than those shown based on the deployment process. The slots or other cutouts may be cut into the spinal cage either before or after stored strain is imparted to the spinal cage.

Figure 8:
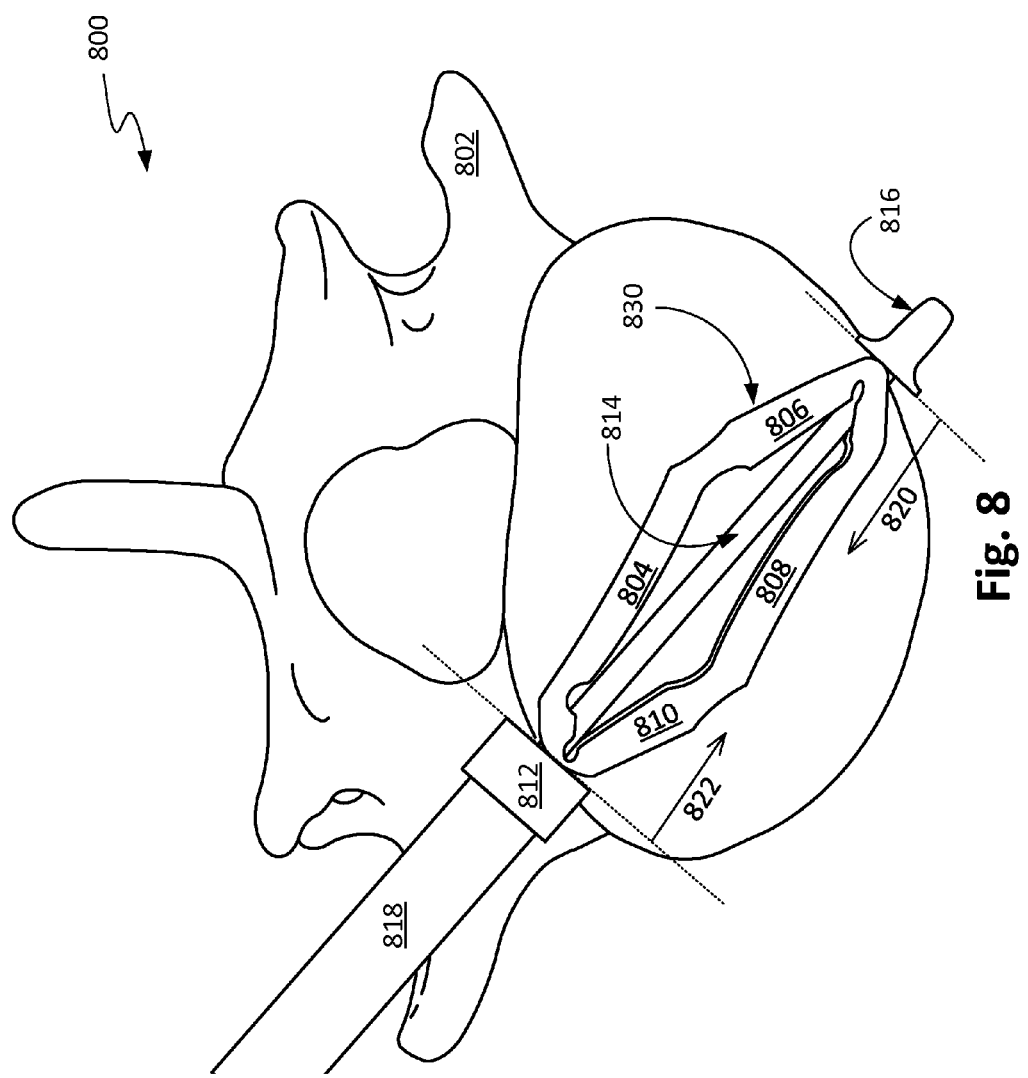
FIG. 8 shows an inferior view of an exemplary embodiment of a TLIF spinal cage through an initial stage of mechanical deployment within an intervertebral space, as placed inferior to a vertebra.

FIG. 8 shows an inferior view of an exemplary embodiment of a TLIF spinal cage through an initial stage of mechanical deployment within an intervertebral space, as placed inferior to a vertebra 802. The surgical processes of inserting and deploying the shape memory polymer spinal cage will be described with respect to these FIGS. 8-10, and is in addition to the previous discussion herein of the details of the shape memory polymer spinal cage.

The spinal cage 830 is inserted through a surgical portal formed for the TLIF procedure, at an angle of roughly 35 degrees to the sagittal plane. Other embodiments of surgical procedures may be used, including adaptations to the spinal cages described herein, as well as the surgical portals used. The surgical procedure leading up to FIG. 8 may be performed with a variety of known surgical techniques. The spinal cage 830 is inserted via one of the known surgical procedures until it is situated in an intervertebral space, as illustrated by the position of the spinal cage below the vertebra 802. At this point in the surgery, the spinal cage 830 may be deployed to its final shape to aid fusion of the vertebrae.

As shown in FIG. 8, the spinal cage 830 has been deployed only through an initial stage of deployment and stored strain recovery as the side walls 804, 806, 808, and 810 of the spinal cage 830 are largely aligned with the insertion axis along the surgical portal as well as the other sides of the spinal cage. The insertion shape of the spinal cage 830 may be similar to that shown or may have the side walls 804, 806, 808, and 810 even further aligned with the insertion axis.

The spinal cage 830 generally deploys by expanding out from the insertion axis as the spinal cage regains a roughly parallelogram shape. For example, the dorsal wall 804 aligns during deployment toward the dorsal portion of the vertebra 802. As shown in this initial stage of deployment, the width of the spinal cage 830 as shown on the page is barely larger than the width of the back plate 812. In addition, the compression rod 814 is still largely outside the insertion rod 818 and has yet to be contracted back into the insertion tool.

The spinal cage 830 has a certain stored strain during insertion into the body, represented in the narrow cross-section of the device that allows surgical installation through the exemplary TLIF surgical portal. Strain is stored in the spinal cage 830 via the shape memory effect of the shape memory polymer. For example, the shape memory polymer is designed, as described further herein, such that the spinal cage will not be subjected to heat or temperatures that cause activation of the shape memory polymer. This may be achieved via selecting a very high activation temperature that is outside a range of expected storage and use temperatures, such as the activation temperature of the described exemplary PEEK shape memory polymer.

Different portions of the spinal cage 830 store strains with different magnitudes and/or directions. For example, the strain stored in the spinal cage 830 will be stored largely in portions of the spinal cage near the junctions between the side walls 804, 806, 808 and 810. There may be some portions of the spinal cage 830 that do not have any stored strains, such as the portions of the side walls 804, 806, 808, and/or 810 that may remain straight throughout imparting of the collapsed shape and deployment of the expanded shape. In addition, different portions of the spinal cage 830 will recover stored strain at different rates and to different extents (e.g., fully, incompletely) during deployment. There may be portions of the spinal cage 830 that retain portions of the stored strain, even after deployment. This may occur due to interactions with the environment, such as reaching a constraint (e.g., bone wall) that limits deployment to the expanded shape. In addition, there may be portions of the spinal cage that have additional strains imparted during deployment, which are separate from the stored strain, thus causing the spinal cage to assume a shape that differs from the expanded shape in some manner.

As described further herein, mechanical activation of the stored strain deployment of the spinal cage 830 occurs based on compressive forces 820 and/or 822. These compressive forces 820 and 822 either have components themselves that oppose a stored strain in a portion of the spinal cage 830, or are translated either by the insertion tool 818 or the spinal cage itself (e.g., via transmission through the spinal cage body) into force components that oppose the stored strain. These forces opposing the stored strain in portions of the spinal cage 830 mechanically activate the shape memory polymer to recover the stored strains at much lower stresses than would be required to impart new strain on the shape memory polymer.

In addition, strains recovered in via mechanical activation affect the mechanical properties of the deployed spinal cage much less than additional strains would be imparted on the device. The mechanical deployment of the shape memory polymer, in contrast, returns the shape memory polymer to an originally-set molecular configuration, which may have significantly different mechanical properties than a strained molecular configuration. For example, the entropy of the molecular configuration of a shape memory polymer portion of the spinal cage 830 that is strained is significantly different from the entropy of that same shape memory polymer portion when it is unstrained (e.g., such as in an expanded, memorized, or unconstrained shape). Thus, as described further herein, release of strain through shape memory activation of the shape memory polymer portion, rather than imparting new strain, also avoids the problem of "spring back" or the tendency for a strained material to recoil from the strain imparted on it.

Through mechanical activation, strains recovered by the shape memory polymer portions in the spinal cage 830 are achieved with lower a force than imparting deformations initially, which simplifies surgery much in the same way avoiding the requirement to activate shape memory polymer portions via heating. In addition, mechanical activation of the spinal cage 830 provides a release of strained molecular configurations that allow the shape memory polymer portions of the spinal cage to reach a state of greater entropy and consistently strong mechanical properties without the impulse to spring back or recoil from newly-applied strains.

As described further herein, storing strain may occur via a shape memory polymer effect whereby the strain is stored via a lack of activation of the shape memory polymer portion. Strain may also exist in a shape memory polymer portion when it is activated against a constraint, whereby the activated recovery of the shape memory polymer portion provides forces against the constraint. However, the storing of strain via the shape memory effect is different than an already-activated shape memory polymer that remains strained due to constraints, such as constraints encountered in the environment of the spinal cage 830, such as the vertebra 802.

Figure 9:
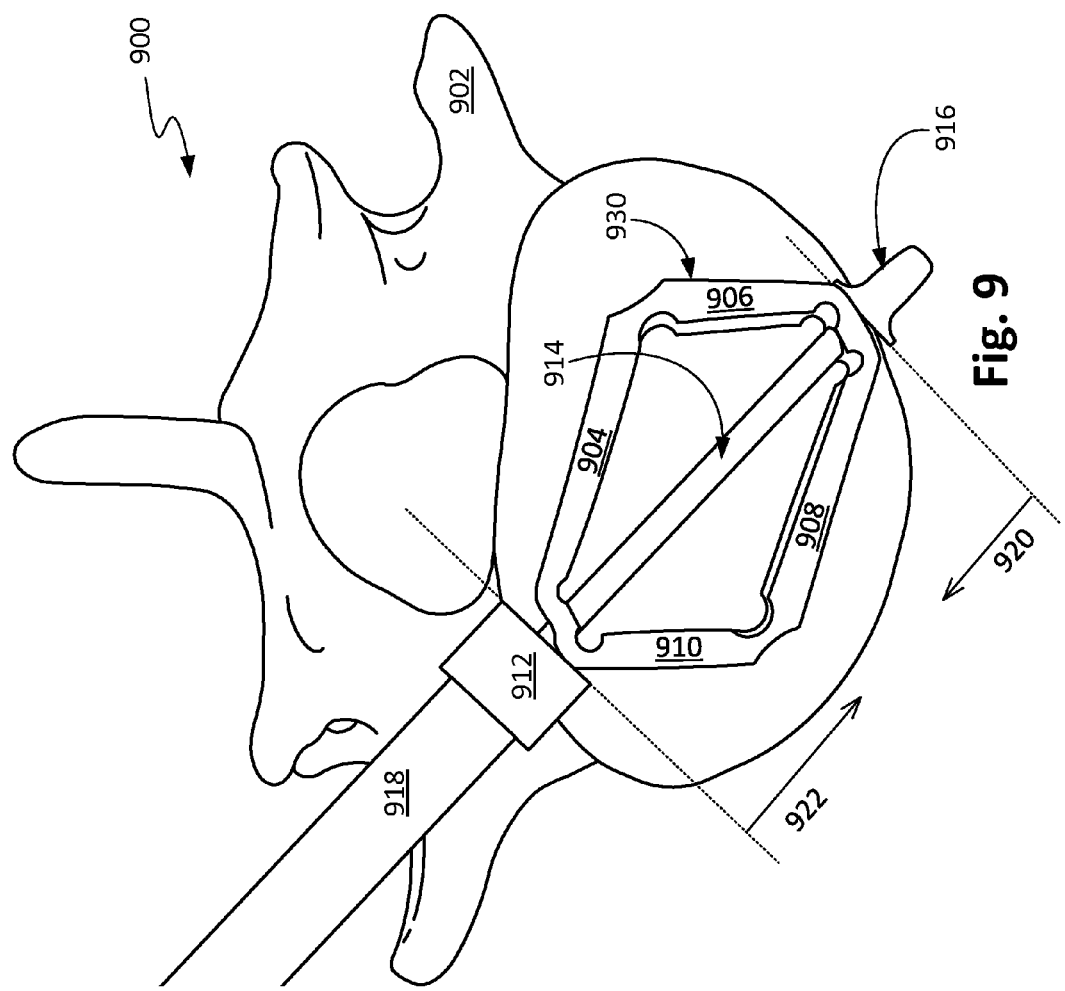
FIG. 9 shows an inferior view of an exemplary embodiment of a TLIF spinal cage recovered through a later stage of mechanical deployment within an intervertebral space.

FIG. 9 shows an inferior view of an exemplary embodiment of a TLIF spinal cage 930 through a later stage of mechanical deployment within an intervertebral space. The side walls 904, 906, 908, and 910 of the spinal cage 930 have moved toward the parallelogram structure of the deployed shape. The dorsal wall 904 has moved toward its final position near the dorsal side of the vertebra 902, while the right wall 906, the left wall 910, and the ventral wall 908 have also moved toward their final position near their respective sides of the vertebra. Mechanical deployment has occurred and may continue to occur via compressive forces 920 and 922 being generated between the insertion tip 916 and the back plate 912 of the insertion tool 918 by the compression rod 914. It will be understood by those skilled in the art that other insertion tools may be used and the specific embodiment of the insertion tool 918 shown in the figure is simplified to illustrate the compressive forces 920 and 922. In addition, it will be understood that other forces may be used to mechanically activate and deploy the shape memory polymer spinal cage 930 and that, as described further herein, the forces used may be transmitted and transformed (e.g., in position, in direction) through the spinal cage to oppose the stored strain in a portion of the spinal cage.

As described further herein, strains stored by the shape memory polymer spinal cage 930 are largely stored in corner portions of the device. Also as described further herein, the semi-circular cutouts of the shape memory polymer portions in and around corners of the spinal cage 930 are included in order to allow further degrees of strain in those portions of the spinal cage than in the side walls 904, 906, 908, and 910.

Mechanical activation of these stored strains also concentrates in and around these corner portions of the shape memory polymer spinal cage 930 during deployment of the spinal cage. When compressive activation forces 920 and 922 are applied to the spinal cage 930, these activation forces may be translated from the point of contact with the insertion tool 918 (e.g., near insertion tip 916, near back plate 912), along the structure of the spinal cage, to the area(s) or portions of the shape memory polymer with stored strain. In addition, as described further herein, the translated forces may be translated in direction in order to be opposed to the stored strain. The difference in stresses required to activate strain recovery versus those required to initiate new strains may be used advantageously to translate the compressive forces 920 and 922 from the insertion tool 918 to the portion of the shape memory polymer with any remaining stored strain and/or to translate the direction of those forces to be in opposition to the stored strain.

Stored strains may also exist in any or all of the side walls 904, 906, 908, and/or 910, in forms such as bending the side walls inwards toward the insertion axis. These stored strains may also be activated by compressive forces 920 and 922 from the insertion tool 918, which may be translated in location or direction through the structure of the spinal cage 930. The stored strains in the shape memory polymer portions of the side walls 904, 906, 908, and/or 910 may activate before, after, and/or simultaneously with activation of recovery of the stored strains in one or more of the corner portions.

The stored strain in certain portions of the shape memory polymer spinal cage 930 may be completely recovered in portions while may remain in other portions. For example, portions of the shape memory polymer spinal cage 930, as shown, such as the dorsal wall 904 may have completely recovered any stored strain (e.g., a slight bending strain shown in FIG. 8) early during recovery from the installation shape to the deployed shape of the spinal cage while there remains significant strain in one or all of the corner regions of the spinal cage. As another example, one corner portion of the spinal cage 930 may become fully recovered (e.g., no stored strain remaining) before another corner portion has all of its strain recovered and while another corner portion is still recovering strain due to continued mechanical activation. Additional mechanical activation may induce, in certain configurations of the spinal cage, new strains into certain portions of the spinal cage 930. These new strains may respond immediately with responsive stresses opposing the strains, and may recoil either elastically or inelastically after mechanical activation has ceased (e.g., compressive forces 920 and 922 being removed). The new strain may also set a new stored strain based on the properties of the shape memory polymer and based on known methods of setting a stored strain in a shape memory polymer near or below the glass transition temperature.

A deployment mechanism for the spinal cage may be adapted to indicate, such as through a length of the compression rod 914 drawn into the insertion rod 918, whether a portion of the spinal cage 930 has completely recovered the stored strain. For example, an insertion tool may indicate that a measured length of the compression rod 914 has been drawn into insertion rod 918 during mechanical deployment of the spinal cage 930. The measured length could indicate or allow the determination that a portion of the spinal cage 930 (e.g., a corner region) has fully recovered the stored strain in that portion. In response to the portion having fully recovered the stored strain in that portion, the decision may be made during surgery to remove the deployment mechanism from the spinal cage 930 and complete the surgery.

Figure 10:
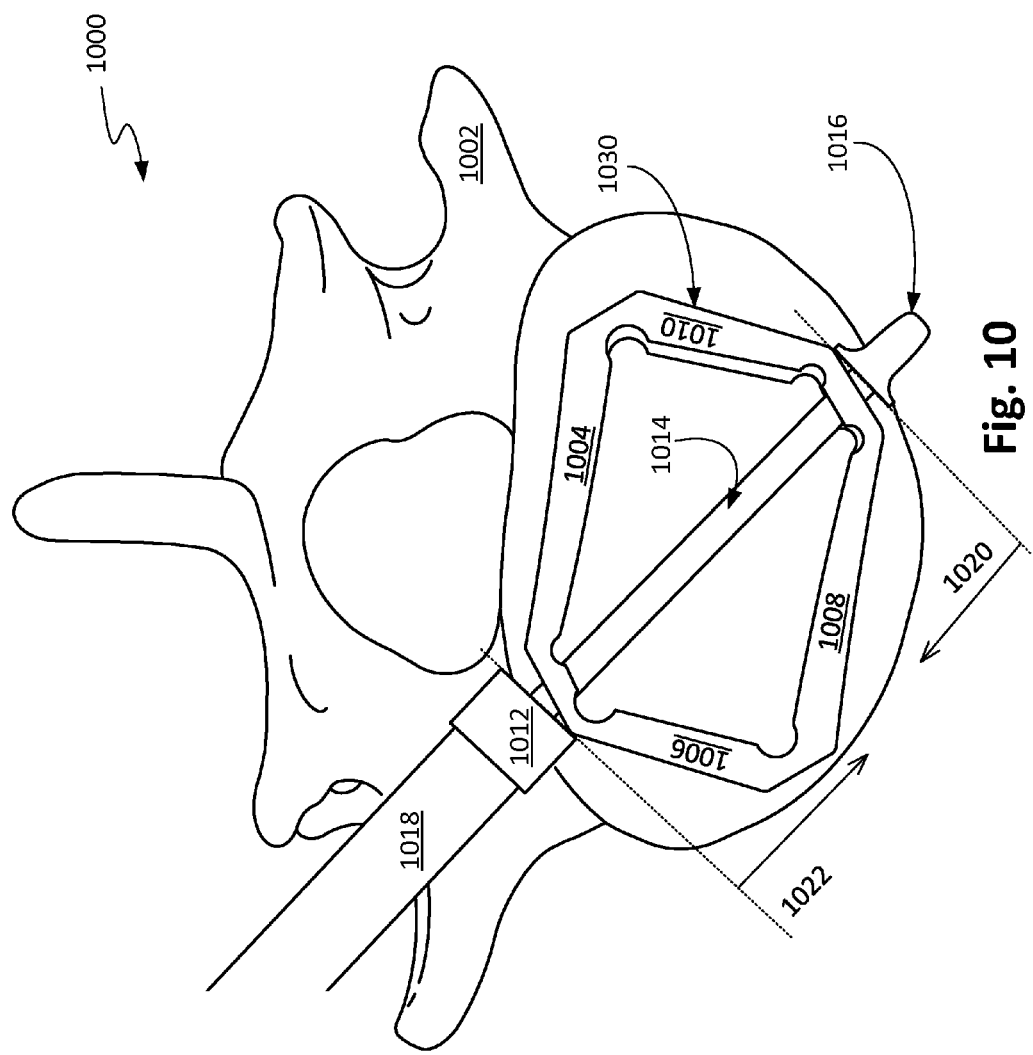
FIG. 10 shows an inferior view of an exemplary embodiment of a TLIF spinal cage recovered through a final stage of mechanical deployment within an intervertebral space.

FIG. 10 shows an inferior view of an exemplary embodiment of a TLIF spinal cage 1030 recovered through a final stage of mechanical deployment within an intervertebral space. The mechanical activation of the shape memory polymer portions of the spinal cage 1030 is nearly complete, and may be completed in certain portions, such as one or more of the side walls 1004, 1006, 1008, and/or 1010. The compressive forces 1020 and 1022 are still applied by the insertion tool 1018 between the back plate 1012 and the insertion tip 1016, but the forces may still be translated and transformed to activate the remaining stored strains. Additional compressive forces 1020 and 1022 may continue to activate any remaining strains as well as may induce further strains into portions of the device. For example, particularly weak or thin portions of the spinal cage may become further strained while portions of the spinal cage are still recovering the initial stored strain from the installation shape. As described further herein, the difference in stresses required to recover strain and impart strain on the shape memory polymer may interact with the particular memorized/unconstrained shape of the spinal cage, thus concentrating the stresses localized in these regions (e.g., sharp bends, narrow sections) caused by the continued compressive forces 1020 and 1022.

As described further herein, the extent of strain recovery possible for the spinal cage 1030 depends on any constraints applied to the spinal cage during deployment. For example, constraints or other interactions with the patient's body (e.g., vertebra 1002) may limit the final shape that can be achieved by the spinal cage 1030. Strains may remain in the spinal cage 1030 due to these constraint(s), even after sufficient mechanical activation has recovered all other stored strains and/or induced further strains in portions of the spinal cage. The further strain induced into the spinal cage 1030 is not shown herein, and will vary based on circumstances. Any further strain is likely to be localized where the applied compressive forces 1020 and 1022 are concentrated into peak areas of stress. These areas may include the corner regions, the straight sections of the side walls, and/or areas in between. However, since the constraints within the surgical process will vary, including the interfaces with the subject vertebrae 1002, the particular configuration of the spinal cage 1030 may vary from the unconstrained shape shown.

It is clear that many modifications and variations of these embodiments can be made by one skilled in the art without departing from the spirit of the novel art of this disclosure. While specific parameters, including device configurations, parameters of components, and thresholds may have been disclosed, other reference points can also be used. These modifications and variations do not depart from the broader spirit and scope of the present disclosure, and the examples cited here are illustrative rather than limiting.

What is claimed is:

1. A spinal cage system, comprising:
a body made of a shape memory polymer with a stored strain, wherein the shape memory polymer has a transition onset temperature above 120 degrees Fahrenheit;
wherein the stored strain comprises a difference in shape between an insertion shape of the body having an insertion axis and a deployed shape of the body adapted to cover a central intervertebral space;
a detachable deployment mechanism that connects with the body along the insertion axis at an insertion-leading portion of the body and at an insertion-trailing portion of the body;
wherein the deployment mechanism is adapted to activate recovery within a plurality of portions of the shape memory polymer only with mechanical forces applied along the insertion axis between the insertion-leading portion and the insertion trailing portion; and
wherein the shape memory polymer is adapted to expand via only thermal expansion below 120 degrees Fahrenheit and without undergoing any shape memory polymer activation.

2. The spinal cage system of claim 1, wherein the deployment mechanism provides mechanical forces without any thermal energy input to the shape memory polymer.

3. The spinal cage system of claim 1, wherein the body contains a stored strain that was set below 120 degrees Fahrenheit.

4. The spinal cage system of claim 1, wherein the deployed shape of the body is in the form of a loop and comprises a ventral portion of the loop and a dorsal portion of the loop, and wherein the insertion shape of the body has the ventral portion and the dorsal portion collapsed toward the insertion axis.

5. The spinal cage system of claim 1, wherein the insertion axis is 35 degrees with respect to the sagittal plane.

6. The spinal cage system of claim 1, wherein the stored strain does not activate over the period of 1 year while packaged at a temperature below 120 degrees Fahrenheit.

7. A method comprising:
shaping a spinal cage from a shape memory polymer with a transition temperature above 120 degrees Fahrenheit;
imparting a stored strain on the shape memory polymer;
forming holes in a vertical wall of the spinal cage along an insertion axis of the spinal cage, the holes adapted to receive a deployment mechanism adapted to provide deployment forces along the insertion axis to activate recovery of the stored strain in the spinal cage; and
storing the spinal cage with the stored strain in a sterile package below 120 degrees Fahrenheit.

8. The method of claim 7, wherein the imparting is performed while the shape memory polymer is below 120 degrees Fahrenheit.

9. The method of claim 7, wherein a transition onset temperature of the shape memory polymer is above 120 degrees Fahrenheit.

10. The method of claim 7, wherein the imparting is performed including:
heating the shape memory polymer to a temperature at or above the transition temperature;
while the shape memory polymer is at or above the transition temperature, straining the shape memory polymer with the stored strain; and
while maintaining the stored strain in the shape memory polymer, cooling the shape memory polymer to below the transition temperature.

11. The method of claim 7, wherein the imparting is performed via straining the shape memory polymer with the stored strain while the shape memory polymer is maintained at a temperature below the transition temperature of the shape memory polymer.

12. The method of claim 7, wherein the imparting is performed via straining the shape memory polymer with the stored strain while a modulus of the shape memory polymer is above 2.5 gigapascals (GPa).

13. The method of claim 7, wherein the forming is performed while the shape memory polymer has a modulus above 2.5 gigapascals (GPa).

14. The method of claim 7, wherein the forming is performed after imparting the stored strain on the shape memory polymer.

15. The method of claim 14, wherein the forming is performed by cutting slots in the vertical wall perpendicular to the insertion axis.

16. The method of claim 7, further comprising:
storing the spinal cage with the deployment mechanism in the sterile package.

17. A method comprising:
receiving a spinal cage formed of a shape memory polymer with a transition onset temperature above 120 degrees Fahrenheit and containing a stored strain defining a difference between an expanded shape and an insertion shape;
inserting the spinal cage in the insertion shape into an intervertebral space along an insertion axis of the spinal cage;
engaging a deployment mechanism with the spinal cage to apply a deployment force to the spinal cage along the insertion axis;
applying the deployment force to the spinal cage along the insertion axis to activate the shape memory polymer to recover the stored strain while the shape memory polymer remains below the transition onset temperature;
wherein the applying the deployment force is performed with the shape memory polymer being below the transition onset temperature; and
removing the deployment mechanism from the spinal cage in the expanded shape while the shape memory polymer is below the transition onset temperature.

18. The method of claim 17, wherein the inserting step is performed with an insertion tool that contains the deployment mechanism and wherein the engaging step is performed before the inserting step.

19. The method of claim 17, further comprising:
determining from an indication from the deployment mechanism that at least a portion of the spinal cage has completed recovery of all strain stored in the portion of the spinal cage;
wherein the removing is performed in response to the determining step.

20. The method of claim 17, wherein the expanded shape covers a majority of an intervertebral space and wherein the insertion shape comprises a cross-section of less than about 1 cm by 1 cm when measured perpendicular to the insertion axis of the spinal cage.

* * * * *